United States Patent
Sherman et al.

(10) Patent No.: US 7,618,820 B2
(45) Date of Patent: Nov. 17, 2009

(54) SYSTEM AND METHOD FOR DETERMINING THE OPERATING STATE OF ORTHOPAEDIC ADMIXTURES

(75) Inventors: Jason T. Sherman, Newark, OH (US); Mark R. DiSilvestro, Fort Wayne, IN (US)

(73) Assignee: DePuy Products, Inc., Warsaw, IN (US)

( * ) Notice: Subject to any disclaimer, the term of this patent is extended or adjusted under 35 U.S.C. 154(b) by 885 days.

(21) Appl. No.: 10/881,802

(22) Filed: Jun. 30, 2004

(65) Prior Publication Data
US 2006/0000284 A1    Jan. 5, 2006

(51) Int. Cl.
*G01C 3/08* (2006.01)
(52) U.S. Cl. .............................. 436/2; 73/587; 73/589; 73/861.23; 264/407; 264/411
(58) Field of Classification Search ................ 73/54.41, 73/592, 64.42, 64.53, 61.79; 366/139, 319, 366/320; 422/225, 102, 58, 68.1; 264/407, 264/411
See application file for complete search history.

(56) References Cited

U.S. PATENT DOCUMENTS

| | | | |
|---|---|---|---|
| 3,413,595 A | | 11/1968 | Ivanovich et al. |
| 4,327,587 A | | 5/1982 | Docekal et al. |
| 4,559,810 A | | 12/1985 | Hinrichs et al. |
| 4,680,958 A | | 7/1987 | Ruelle et al. |
| 4,854,716 A | * | 8/1989 | Ziemann et al. ............. 366/139 |
| 4,862,384 A | | 8/1989 | Bujard et al. |
| 4,921,415 A | | 5/1990 | Thomas, III et al. |
| 5,187,980 A | | 2/1993 | Blair et al. |
| 6,020,396 A | | 2/2000 | Jacobs |
| 6,227,040 B1 | * | 5/2001 | Hastings et al. ............. 73/54.41 |
| 6,296,149 B1 | | 10/2001 | Long |
| 6,491,635 B1 | | 12/2002 | Mazess et al. |
| 6,644,122 B2 | | 11/2003 | Borowczak et al. |
| 6,736,537 B2 | * | 5/2004 | Coffeen et al. ............... 366/130 |

FOREIGN PATENT DOCUMENTS

| | | |
|---|---|---|
| DE | 100 08 481 A1 | 9/2001 |
| EP | 0 995 981 A2 | 4/2000 |

OTHER PUBLICATIONS

Viano, A.M. et al., "Ultrasonic Characterization of the Curing Process of Hydroxyapatite Modified Bone Cement," Journal of Biomedical Materials Research, 56(4), 593-599 (2001).
Nilsson, M. et al., "Monitoring the Setting of Calcium-Based Bone Cements Using Pulse-Echo Ultrasound", Journal of Materials Science: Materials in Medicine, 13 (2002), pp. 1135-1141.

* cited by examiner

*Primary Examiner*—Jill Warden
*Assistant Examiner*—Dwan A Gerido
(74) *Attorney, Agent, or Firm*—Maginot, Moore & Beck

(57) ABSTRACT

A system and method for determining the operating state of a curable composition utilizes an acoustic wave or signal transmitted into a container holding the composition. In one embodiment, characteristics of a reflected component of the acoustic signal are measured and correlated to pre-determined values indicative of one or more operating states, or degrees of curing, of the composition. In another embodiment, characteristics of a transmitted component of the acoustic signal are measured and correlated. The characteristics include, for example, the speed of sound through the curable composition or the attenuation of the acoustic signal reflected by or transmitted through the composition.

24 Claims, 2 Drawing Sheets

SYSTEM AND METHOD FOR DETERMINING THE OPERATING STATE OF ORTHOPAEDIC ADMIXTURES

BACKGROUND OF THE INVENTION

The present invention relates to the preparation of orthopaedic mixtures and compounds, such as bone cement. More specifically, the invention concerns systems and methods for identifying the operating state of these compounds, such as the degree of cure of bone cement.

It is necessary in many orthopaedic surgical procedures to employ a cement or grouting type agent, such as for attaching artificial joint implants to bone, repairing or forming joints in bones, or other forms of orthopaedic work. The type of cement used typically depends upon many factors, including the type of implant, the manner of application, the amount of working time required, etc. While many types of bone cement are available, most of the cements used for orthopaedic purposes include a self-curing resin formed from the blending of a wide variety of liquid monomers or co-monomers with powdered polymers or copolymers to form a viscous admixture to be used as the grouting agent. Most bone cements are acrylate-based compositions formed of a liquid component and a powder component. A typical liquid component is a liquid mixture of a monomeric methyl methacrylate. The powder component generally consists of a methylmethacrylate-styrene copolymer. Curing of the liquid-powder composition occurs as the constituents polymerize and cross-link.

The admixture of the powder and liquid components develops a quick setting material. As such, preparation of the cement usually occurs directly within the operating area just prior to use. In particular, a bone cement mixing apparatus is generally utilized to mix the powder and liquid components in the operating area. The resultant admixture is then removed from the mixing apparatus and placed in a cement delivery apparatus for subsequent use by the surgeon. Specifically, the bone cement must generally first be scooped or otherwise removed from the mixing apparatus and thereafter placed in a syringe-type delivery apparatus for use by the surgeon. In other cases, the bone cement components are mixed directly in the delivery apparatus, which eliminates the need to transfer the bone cement from a mixing apparatus to the syringe-type delivery system.

Bone cements typically have setting times between 6½ to 15 minutes. Three operating points characterize the curing of bone cement. The dough time, distinguished qualitatively as the point in time where bone cement no longer sticks to latex gloves, is the first operating point. The dough time, which is measured relative to initial mixing, occurs after the mixing of the bone cement. The dough time is significant as it is identified as the start point of the working time of the admixture. The working time encompasses the amount of time during which the viscosity or flowability of the composition is sufficient to allow introduction of the composition into the surgical or implant site. The end of working time, distinguished qualitatively as the point in time where bone cement no longer sticks to itself, is the second operating point. The end of work time is relative to initial mixing and signifies that the working time has ended and the bone cement should no longer be used in the surgery. The third operating point is the setting time, which is the time relative to initial mixing at which the bone cement admixture hardens or sets sufficiently to hold the prosthesis within its implant site.

Since the overall setting times for most orthopaedic compositions, such as bone cements, are short, it is important that the composition be introduced into the implant site as soon as practicable. For many compositions, the admixture must reach a certain level of cure to have the viscosity, flowability or malleability to allow the material to be properly introduced into the surgical site. For instance, many orthopaedic implants include a stem that is fixed within the intramedullary canal of a bone, such as the femur. As a precursor, bone cement is injected into the prepared intramedullary canal prior to introduction of the implant stem. Optimally, the bone cement flows into porous recesses of the bone to ensure a solid mechanical interlock with the implant. If the bone cement is administered before the appropriate degree of cure, the cement will be too fluid, which may make it difficult to properly administer. Moreover, if the bone cement is too fluid, it may overflow upon application or when the implant stem is introduced.

On the other hand, if the cement has cured too much, it may be too viscous so that it does not fill the bone voids and interstices. This can result in a poor mechanical interlock or interface between implant and bone. Even if the composition is viscous enough for proper application, it may cure in situ to a point that prevents proper positioning and alignment of the implant stem within the bone. An even greater degree of cure will render the bone cement too viscous to be usable.

Bone cement failure is believed to be a primary mechanism for loosening of prosthetic joint components. It can be readily appreciated that it is very desirable to accurately determine the degree of cure or operating state of the composition in the surgical arena so that the composition can be applied at the optimum point in its curing cycle. One ASTM standard relies upon determining the resistance to a plunger pushed into a container of curable material. A similar approach is disclosed in European Patent Publication EP0995981 in which a predetermined discharge force is applied to a bone cement reservoir and the travel distance of bone cement through a test lead is measured. This testing approach is cumbersome, susceptible to measurement error and not conducive to being repeated as the bone cement cures.

In another approach, an electric current is passed through a bone cement sample. Variation in an electrical property of the bone cement, such as capacitance, is used to determine the amount of cure of the material. (See, e.g., Aesculap German application DE10008481) One drawback with this approach is that it is equipment intensive. Moreover, this approach requires the composition to not only have measurable electrical properties, but also that the electrical properties vary as a function of the cure of the material.

There is a need for a system and method for accurately determining the operating condition or degree of cure of a biological composition, such as bone cement. The need is also felt for such a system that can be used with the composition as it exists in the surgical setting. This need further extends to a reusable system that requires minimal or no redesign of current delivery systems.

SUMMARY OF THE INVENTION

In order to meet these needs, the present invention contemplates a system and method that relies upon the acoustic properties of the biocompatible composition or admixture. More specifically, the invention resides in exposing the composition in a container, such as an application delivery system, to an ultrasonic signal. Changes in the acoustic properties of the composition can be correlated to changes in its degree of polymerization or cure. The acoustic properties can be based on reflectance and transmittance of the acoustic signal and can include, by way of non-limiting example, the speed of sound through the composition, attenuation of the signal amplitude, attenuation of the amplitude over time, frequency shift, attenuation of a frequency metric over time, acoustic impedance, as well as any order derivatives as a function of time of these properties. All of these properties can be related either to the admixture alone or to the admixture-delivery system composite.

In accordance with the invention, the admixture is prepared and stored in a delivery device that will be used to apply the admixture to the surgical site. The delivery device is formed of a standard material, such as polypropylene or glass, which permits passage of acoustic signals. An ultrasonic transducer is mounted to the wall of the delivery device. In one embodiment, the transducer includes a receiver array to receive reflected ultrasonic signals. It is known that the interface between dissimilar materials will produce a reflection of an acoustic signal. Thus, this embodiment contemplates reflected signals from the wall-composition interfaces adjacent the ultrasonic sensors (near wall reflectance) and on the delivery device wall opposite the transducer (far wall reflectance). This embodiment also contemplates reflected signals from the wall-air interface opposite the transducer (far air reflectance). As the composition cures, its physical properties change, which results in a change of reflectance at the wall-composition and wall-air interfaces. An empirical relationship between near wall, far wall, and far air reflectance values and the degree of cure of the composition can be derived and compared to the test values to provide a real-time determination of the operating point of the composition. This empirical relationship can be based on the change in the speed of sound, or some other measured or calculated parameter, through the material as a function of time.

In another embodiment, the ultrasonic wave passes from the transducer, through a couplant, then through the delivery device wall and composition to a sensor mounted on the opposite wall of the delivery device. In this embodiment, the change in transmittance of the admixture or the admixture-delivery device composite is evaluated. In particular, the speed of sound, or some other measured or calculated parameter, can be measured and correlated to empirical data relating composition operating point to the measured or calculated parameter.

It is one object of the invention to provide a system and method that provides an accurate real-time measurement of the degree of polymerization or cure of a bio-compatible composition, such as bone cement. It is another object of the invention to obtain such a measurement without disturbing the composition in its application apparatus.

It is a further object of the invention to be able to identify the three key operating points of bone cement—dough time, end of work time, and setting time—and to relay these points to the orthopaedic surgeon using a simple display method during surgery. Such a display device may be affixed to the delivery system, may be integrated with already existing computer technologies, or may be a stand-alone display. It is contemplated that a simple red, yellow, green LED display will suffice to present the operating points of the bone cement to the surgeon. It is also contemplated that a prediction of the end of work time taking into consideration environmental variables, such as relative humidity and temperature, would be provided to the surgeon. Such a prediction can be based on laboratory data along with data measured from the display device. It is therefore envisioned that the device will present a countdown in some time unit to the surgeon after the dough time has been identified so that the surgeon has a real-time estimate of the end of work time during use of the bone cement. When the end of work time has been identified, it will be displayed to the surgeon so that the bone cement is not used outside of the working time. Such a display method will increase the utility of the contemplated system.

Other objects and specific benefits of the invention will become apparent upon consideration of the following written description taken together with the accompanying figures.

DESCRIPTION OF THE PREFERRED EMBODIMENTS

Figure 1:
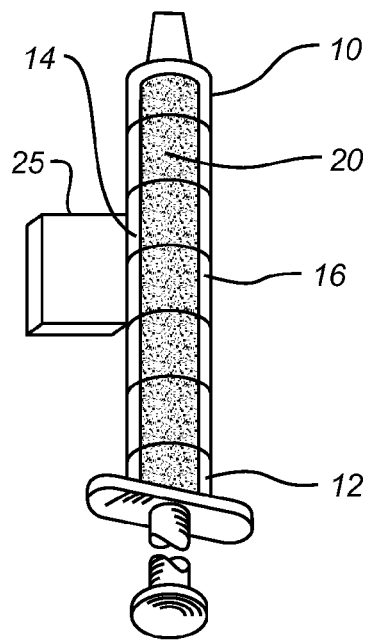
FIG. 1 is a side perspective view of a delivery device carrying a curable composition with an ultrasonic transducer apparatus mounted thereto in accordance with one embodiment of the present invention.

For the purposes of promoting an understanding of the principles of the invention, reference will now be made to the embodiments illustrated in the drawings and described in the following written specification. It is understood that no limitation to the scope of the invention is thereby intended. It is further understood that the present invention includes any alterations and modifications to the illustrated embodiments and includes further applications of the principles of the invention as would normally occur to one skilled in the art to which this invention pertains.

Referring to FIG. 1, a delivery device 10 is shown carrying a supply of a curable composition 20. In the preferred embodiment of the invention, the composition 20 is a curable biomaterial or bio-compatible material, such as bone cement. The composition 20 is curable, meaning that it changes operating state or physical properties over time. For instance, a typical bone cement, such as polymethylmethacrylate, polymerizes over time so that the viscosity or flowability of the composition gradually changes until the composition is fully hardened.

The delivery device 10 may be any container suitable for containing a bone cement mixture as it cures. More particularly, the container is suitable for delivering the composition to a surgical site, such as into the intramedullary canal of a bone in preparation for receiving the stem of a prosthesis. In accordance with the present invention, the delivery device must permit passage of acoustic signals, or more specifically ultrasonic signals, and should have stable acoustic properties. Most preferably, the delivery device is a syringe that includes a barrel 12 within which the composition 20 is contained. While the barrel 12 is cylindrical, for purposes of understanding the present invention it is presumed that the barrel includes a proximal portion 14 and a distal portion 16 that is generally diametrically opposite the proximal portion. The syringe barrel is typically formed of a plastic material that has known physical properties for transmission of acoustic signals that can be readily quantified for use with the present invention.

Figure 3:
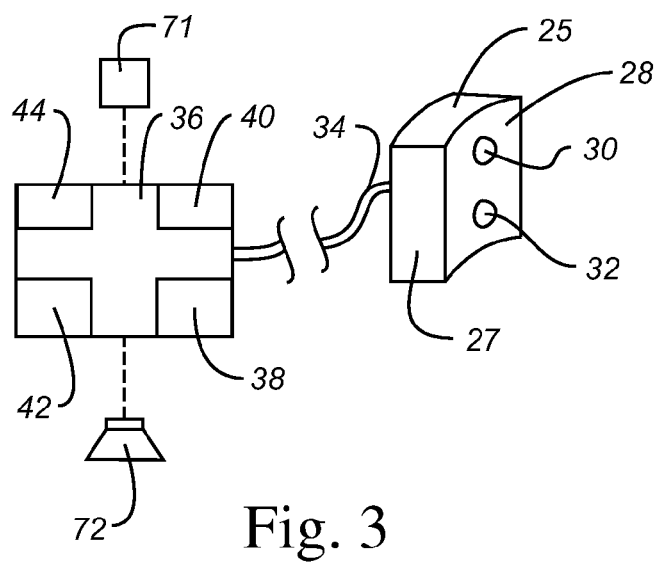
FIG. 3 is a schematic representation of the transducer apparatus and associated processor.

In accordance with one embodiment of the invention, an acoustic generator and sensor assembly 25 is associated with the delivery device 10. As shown in FIG. 3, the assembly 25 includes a body 27 that is configured to be held flush with the barrel 12 of the composition delivery device. Thus, one surface 28 of the body 27 can be curved to match the curvature of the barrel at the proximal portion 14. Additionally, if slight modification of the delivery device is advantageous and minimizes the system design, the delivery device can be modified so that parallel and opposing flat surfaces are created across the diameter of the body. Also, if the radius of the barrel 12 of the delivery device 10 is large enough with respect to the size of the ultrasound transducer, a flat-faced transducer may be used without degradation in performance. The body can be provided with some means to hold the body on the barrel. For instance, the curved surface 28 of the body can be provided with a removable adhesive. Alternatively, a clip or strap (not shown) can be associated with the body 27 and configured to engage the barrel to hold the surface 28 in flush contact with the barrel. An acoustic couplant, such as a gelatinous material, may be necessary to ensure proper acoustic signal propagation from the ultrasound transducer into the delivery device-admixture composite and proper reflection back to the transducer. Thus, a gelatinous material (not shown) is preferably interposed between the body 27 of the assembly 25 and the barrel 12.

In the present embodiment, the assembly 25 relies upon sensing a reflected acoustic signal. Thus, the body 27 carries an acoustic emitter 30 and an acoustic sensor 32. Most preferably, the emitter and sensor are adapted for ultrasonic signals, such as in the range of 100 kHz-20 MHz. The emitter 30 is an ultrasonic transducer of known design, such as a piezoelectric transducer, capable of generating an ultrasonic signal of a fixed or variable frequency. The sensor 32 is also of conventional design, such as a sensing transducer that is tuned to a specific frequency or frequency band. Alternatively, the same emitter can perform transmission and sensing functions through the use of known switching circuitry. For purposes of illustration, the ultrasonic emitter and sensor for use with the present invention can be configured as described in U.S. Pat. No. 6,491,635, to Mazess et al. The bone densitometer disclosed in the '635 Patent includes transmitting and receiving transducer arrays and associated circuitry to excite or sample a particular transducer in the array. The description of the transducers and associated control circuitry, and particularly the description associated with FIGS. 4 and 6 of the '635 Patent are incorporated herein by reference. Of course, other ultrasonic measurement systems are contemplated that can meet the physical requirements of the system of the present invention.

The emitter and sensor are sized according to the size of the delivery device, and their relative spacing by the amplitude of the acoustic signal. Preferably, the emitter and receiver are immediately adjacent so that the reflected acoustic signal will strike the sensor 32. By way of non-limiting example, for use with a typical syringe delivery device 10, the body 27 occupies an area on the order of 1.0 sq.in.

Figure 2:
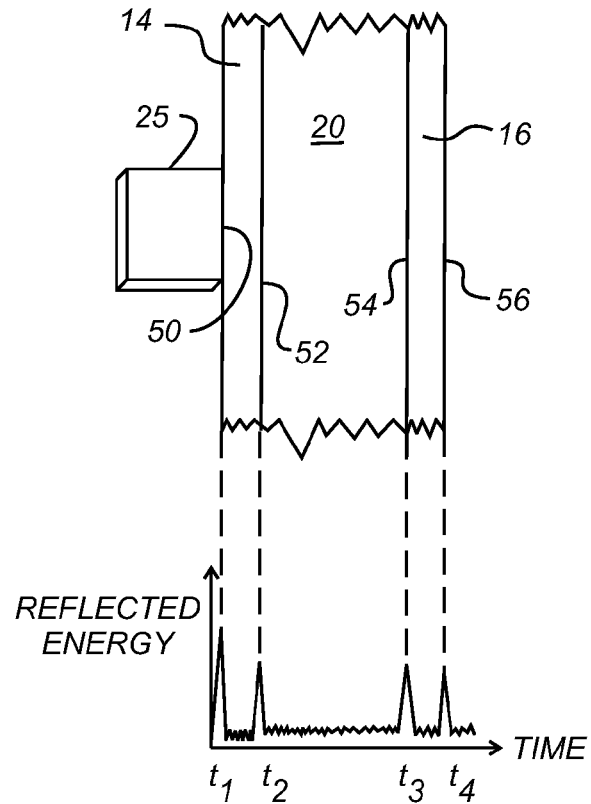
FIG. 2 is a partial cross-sectional view of the delivery device and transducer apparatus shown in FIG. 1, with the reflective interfaces identified and with a sample graph of reflected energy as a function of time superimposed thereon. (Note that the dashed lines in FIG. 2 indicate corresponding interfaces of reflected signals.)

In accordance with the embodiment of FIG. 1, the apparatus 25 relies upon an ultrasonic signal emitted by transducer 30 into the syringe barrel 12 and bone cement composition 20 within. It is known that a portion of an acoustic or ultrasonic signal will reflect at the interface or boundary between dissimilar materials. In the context of the present invention, four such interfaces exist, as depicted in FIG. 2, including: apparatus-proximal portion interface 50; proximal portion—curable composition interface 52, composition—distal portion interface 54; and distal portion—air interface 56. (It can be noted that this last interface 56 can be augmented by a reflective plate mounted to the distal portion 16).

Each interface will produce a reflected signal from the basic signal transmitted by the emitter 30. A representation of the reflected signal as a function of time and interface location is provided in FIG. 2. It can be seen that the intensity or amplitude of the reflected signal decreases at each interface and that the time for the reflected signal to be received by the sensor 32 increases, as expected.

The reflected signal received by the sensor 32 provides a measure of the operating condition of the composition 20 between the proximal and distal portions 14, 16. It is known that the acoustical transmission properties of the curable composition 20 will change over time. This change in transmission properties can be the result of changes in density or in the increase/decrease of scattering particles. Changes in material density will alter the speed of sound through the medium, while the presence of scattering particles will alter the amplitude of the acoustic signal. Sensed changes in the transmission/reflection of the acoustic signal can be correlated to changes in acoustic properties of the composition, which in turn can be correlated to a current operating condition of the composition.

In this embodiment of the invention, the apparatus 25 is electrically coupled by wiring 34 to a processor 36. This processor includes an amplifier 38 that electrically activates the ultrasonic transducer 28 and a sampling circuit 40 that samples an electrical signal generated by the sensor 32 in response to a reflected acoustic signal. The sampling circuit can include an A/D converter to provide a digital signal that can be more readily processed. A microprocessor and/or digital signal processor 42 receives the digital signal from the sampling circuit 40 and generates an output for a display 44 indicative of a sensed condition of the composition.

The microprocessor 42 is calibrated to evaluate the output of the sensor 32 as it relates to the degree of cure, for instance, of the composition. In accordance with this embodiment, the sensor 32 receives reflected signals from each of the interfaces 50-56. Since the acoustic properties of the barrel 12 of the syringe 10 do not change, any change in the reflected acoustic signal can be directly attributed to changes in the physical properties of the composition. In one specific feature of this embodiment, the processor 36 can be calibrated to evaluate the second and third reflected signals from the interfaces 52 and 54, and more specifically the time difference between these two signals. Since the distance between the interfaces 52 and 54 is known (i.e., the diameter of the syringe barrel), the difference between the times $t_3$ and $t_2$ is directly related the speed of sound through the composition 20. The microprocessor 42 can make this calculation each time the emitter 30 transmits an ultrasonic signal—i.e., for each chirp. This time differential can be compared to an empirically obtained differential value that corresponds to a preferred degree of cure, or preferred operating point of the composition 20. Alternatively, the difference between the times $t_4$ and $t_1$ is directly related the speed of sound through the admixture-delivery device composite. As the acoustic properties of the delivery device are stable, the only change in this parameter will be due to changes in the admixture. The microprocessor can be calibrated to evaluate the output of this calculation as described above.

When the measured time differential matches or falls within a pre-determined range of the empirical value, the microprocessor 42 can generate a signal to the display 44. The display 44 can constitute a visual indicator, such as an LED that illuminates when the appropriate operating point has been achieved. A series of LEDs can be provided that are illuminated at different stages of the composition operating state—i.e., when the measured time correlates with empirical values corresponding to the different operating states of the composition. The indicator can be integrated into the apparatus 25 so that it is associated with or mounted on the container or delivery device 10, and therefore immediately at hand. An audible signal can replace or augment the visual indicator.

The processor 36 can be configured at different degrees of sophistication. In its simplest form, the processor activates the emitter 30 at a pre-determined interval that is preferably, but not necessarily, greater than the greatest reflectance time $t_4$, so that no intervening reflected signals from interfaces 50 or 52 will interfere with the signal reflected from the interface 54. This chirp interval will typically be measured in milliseconds. Where the same transducer is used as an emitter and a receiver, the processor will include a switch that changes the mode of the emitter 30 from transmitter to receiver after a chirp signal has been sent, and from receiver to transmitter once the last reflected signal has been received at time $t_4$. As the reflected signals are received, the processor counts the signals and measures the time delay from the transmission of the basic ultrasonic signal. The processor can measure the delay from receipt of the second reflected signal at time $t_2$, or can continuously measure all of the time intervals $t_1$-$t_4$ and then calculate the pertinent differential $t_3$-$t_2$, or $t_4$-$t_1$.

In a more sophisticated system, the processor 36 is configured to evaluate the amplitude, or ultimately the attenuation, of the signal reflected at any or all of the interfaces 52, 54 and 56. As depicted in the graph in FIG. 2, the amplitude of the reflected signal decreases at each of the interfaces. Again, since the material of the syringe barrel is known and unchanging, the attenuation at the first and last reflection interfaces is also known and quantifiable. However, amplitude of the reflected signal at the interfaces 52 and 54 depend upon the properties of the composition 20. Changes in the amplitude of the reflected signal from either of these interfaces can be compared to empirically derived data based on reflective attenuation for different composition operating conditions or cure amounts. The microprocessor 42 can store this empirically derived data and compare the real time amplitude of a selected reflected signal. Alternatively, changes in all of the reflected signals can be analyzed by the microprocessor and averaged or normalized for comparison to a pre-determined value indicative of the optimum operating condition of the composition.

In a very similar embodiment, the delivery device may also contain an inner barrel that may be used for mixing. The principles of the described embodiment are unaffected, although the reflecting interfaces will change and data analysis must be adjusted accordingly.

Figure 4:
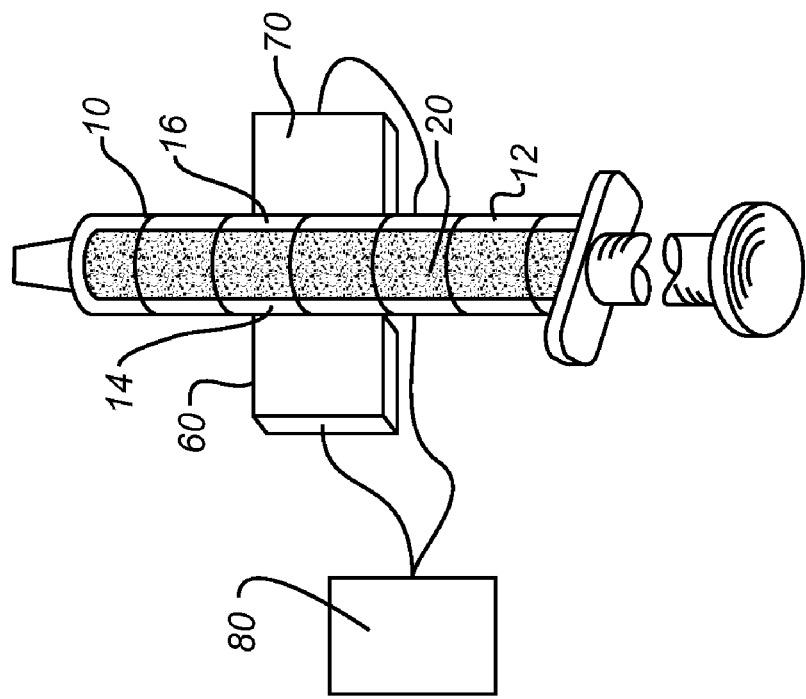
FIG. 4 is a side perspective view of a delivery device carrying a curable composition with an ultrasonic transducer and receiver apparatus mounted thereto in accordance with a further embodiment of the present invention.

In an alternative embodiment, the system relies upon the propagation of the ultrasonic signal through the composition. Thus, as depicted in FIG. 4, an emitter 60 is coupled to the proximal portion 14 of the syringe barrel 12 and a sensor 70 is coupled to the distal portion 16. The two transducers 60, 70 can be coupled to the delivery device in any manner sufficient to removably support them on the delivery device. Thus, the two components can utilize the removable adhesive, clip or strap approaches described above. The emitter and receiver can be piezo-electric transducers or other devices capable of sending and receiving ultrasonic signals.

In accordance with this embodiment, the emitter 60 transmits an ultrasonic signal toward the sensor 70 and through the syringe barrel 12 and composition 20. The transmission properties of the material forming the barrel are fixed and known, while the propagation properties of the composition are variable. Nominally, the acoustic signal is attenuated as it travels through the three layers, although most of the attenuation occurs as the ultrasonic signal propagates through the composition 20, is shown in the graph in FIG. 5. Each transmitted ultrasonic signal or chirp delivered by the emitter 60 will attenuate generally in accordance with this curve and will travel from the emitter 60 to the sensor transducer 70. The amount of attenuation and the propagation time will vary as the physical properties of the composition changes.

A processor 80, similar in construction to the processor 36, controls the activation of the emitter and the evaluation of the signal received from sensor transducer 70. Thus, the processor 80 controls the time interval at which the ultrasonic chirp is transmitted and measures the time delay before the sensor 70 acknowledges that the propagated signal has been received. If the transmission time is used as the quantitative measure of the change in operating condition of the composition, then the amplitude or amount of attenuation of the signal need not be evaluated. In this instance, an A/D converter is not necessary. On the other hand, if signal attenuation is used as the quantitative measure, then the sensor signal can be fed through an A/D converter to provide a digital representation of the amplitude of the propagated signal. The absolute amplitude or the incremental change in amplitude, or any order derivative of the amplitude signal with respect to time can be used as the trigger point, depending upon the nature of the empirical data used for comparison.

With either of the illustrated embodiments, the processor 36, 80 will compare data acquired in real-time as the composition is curing with stored data indicative of the operating points of the curable composition. As explained above, bone cements begin polymerizing or curing as soon as the liquid and powder constituents are mixed. The working time—i.e, the time during which the composition can be applied in the surgical setting—commences at the end of the dough time and continues until the end of working time, Thus, for most curable materials, such as bone cement, at least two operating points are important—the dough time and the end of the working time. The stored data will optimally include data for both operating points. Of course, other operating points, such as setting time, can also be maintained by the processors 36, 80. It is contemplated that the processor may contain complete time-dependent data sets for a number of bone cement samples, and that it will contain an algorithm for comparing the current sample to those samples stored so that the end of working time can be predicted (or otherwise estimated) in real time as the bone cement is used. In particular, a predicted amount of time remaining until the working time of the composition is reached can be generated based on such comparison. And a visual indication of such predicted amount of time remaining can then be visually displayed on a display device 71 (see FIG. 3). Alternatively (or additionally), the predicted amount of time remaining until the working time of the composition is reached may be audibly generated via a speaker 72 (see FIG. 3).

One benefit of this invention is that it can be used to identify the dough time, end of working time, and setting time, and then to relay this information to the orthopaedic surgeon during surgery using a display. An array of indicators can be used to indicate the current operating condition of the bone cement. For instance, a differently colored LED can be activated by the processors at the dough time, end of working time and setting time so that the surgeon has an immediate indication of the bone cement condition.

In certain specific embodiments, the stored data includes only the pre-determined operating point values. In other words, if a transmission system is used, as shown in FIG. 4, the time delay value corresponding to the dough time for the composition is stored and compared against the real-time delay values calculated by the processor 80. Alternatively, a table look-up or an algorithm can be utilized to ascertain a degree of cure throughout the entire curing process. In accordance with the illustrated embodiments, an ultrasonic signal is transmitted at pre-determined intervals on the order of milliseconds in length. Thus, for a one minute dough time, several hundreds of measurements will be made. Each measurement can be compared to the table look-up to ascertain the degree of completion of the dough time, and can even determine an increase or decrease in curing rate.

It is contemplated that the various data points indicative of the operating points or degree of curing of a particular composition will be derived empirically. For instance, test samples of a PMMA bone cement are subjected to a conventional viscosity test, or qualitative testing for identification of the dough time, end of working time, and setting time at pre-determined intervals will be performed. The same sample is simultaneously subjected to testing in accordance with an embodiment of the present invention. The acoustic response value generated by the present invention is then correlated to the conventionally derived viscosity value or operating point if measured directly. Repeating this test at the pre-determined time intervals will map a particular result using the present invention to a known operating point of the composition. These experiments will need to be performed for a variety of bone cements both with and without antibiotics, and in variable environmental conditions.

It is further contemplated that different materials may require different evaluation protocols using the systems and methods of the present invention. For instance, certain compositions may respond more effectively to acoustic signals in a certain frequency range. In other cases, it may be necessary to subject the composition to ultrasonic signals at different frequencies throughout the evaluation process. Applying an ultrasonic signal across a frequency spectrum can be used to increase the accuracy of the operating point evaluation. Additionally, it may be advantageous to measure or calculate one acoustically-dependent parameter for a given bone cement, and an entirely different parameter for another bone cement.

The present invention contemplates that the transducer components 25, 60 and 70 will be "universal", meaning that they can be used on a wide array of delivery devices. The transducer(s) can be mounted to the delivery devices in the manner described above, or can be integrated into a fixture that supports the delivery device and holds it in proper relationship to the transducer(s). The processors 36, 80 can be integrated with the transducer(s) but are preferably separate from the emitter and sensor devices. The processor itself can be formed as an integrated circuit or chip that is connected to the transducer(s) during use. The chip can be provided with the curable composition, with the necessary pre-determined data points "hard-wired" into the chip. Alternatively, the chip can constitute a data chip that is connected to a separate stand-alone processor.

The present invention contemplates, in effect, measuring the acoustic properties, and changes thereof, of the curable material and equating those changes to a known operating condition or state of cure of the material. In one embodiment, the absolute magnitude of an acoustic property is measured. In the illustrated embodiments above, the magnitude includes the amplitude or intensity of the acoustic signal or wave. Alternatively, the magnitude can constitute the speed of sound through the medium. The speed of sound can be measured and used as the basis for determining the composition operating state. Where the acoustic signal being measured is the reflected signal depicted in FIG. 2, the sound velocity through the curable composition is given by the equation:

$$v = 2*d/(t3-t2)$$

where d is the distance between the cylinder wall portions 14 and 16.

Figure 5:
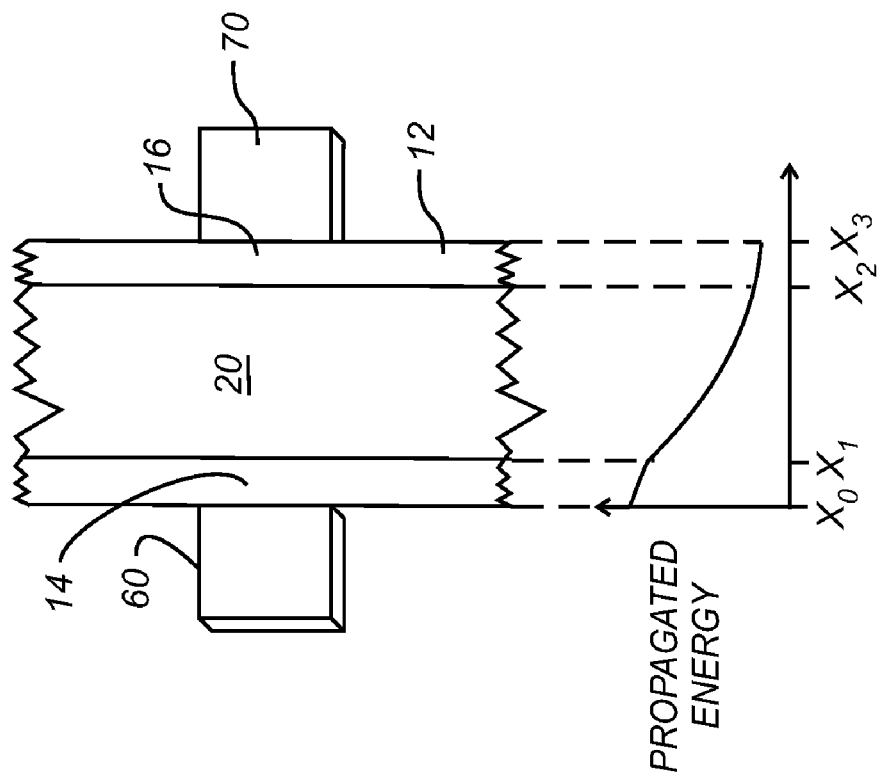
FIG. 5 is a partial cross-sectional view of the delivery device and transducer apparatus shown in FIG. 4, with the transmission interfaces identified and with a sample attenuation graph as a function of distance superimposed thereon. (Note that the dashed lines in FIG. 5 indicate corresponding interfaces of reflected signals.)

On the other hand, where the approach of FIGS. 4-5 is used, based on the acoustic signal transmission, the sound velocity is given by the equation:

$$v = \frac{d2}{\left(t - \frac{d1}{v_{wall}} - \frac{d3}{v_{wall}}\right)}$$

where d2 is the distance between the wall portions 14 and 16, d1 is the thickness of the wall portion 14 and d3 is the thickness of the wall portion 16, and t is the transmission time through the admixture-delivery device composite.

In accordance with one embodiment of the invention, the absolute magnitude of the sound velocity can be compared at different times to determine the operating state of the composition. Alternatively, the changes in sound velocity (or any other acoustic property being used for the evaluation) can be calculated and assessed in relation to the degree of cure of the material. For example, the first derivative of the sound velocity through the composition as a function of time can be calculated and compared to empirically derived data to determine the composition operating state. Depending upon the acoustic parameter and the manner in which it changes with composition curing, any order derivative as a function of time or combination thereof, or any other mathematical calculation can be performed and evaluated. Other acoustic properties can be evaluated using the transducer apparatus and processor of the present invention, including by way of non-limiting example, frequency shift through the composition, attenuation of a frequency metric over time, acoustic impedance, and signal attenuation over time (i.e., changes in the signal strength when measured at different times). It is understood that the processor 36, and particularly the microprocessor 42, can be programmed to calculate and evaluate any of these acoustic properties. It is also understood that whatever acoustic property is used as the measure, comparable empirical data must be stored in the processor for comparison.

While the invention has been illustrated and described in detail in the drawings and foregoing description, the same should be considered as illustrative and not restrictive in character. It is understood that only the preferred embodiments have been presented and that all changes, modifications and further applications that come within the spirit of the invention are desired to be protected.

What is claimed is:

1. A method for determining the operating state of a curable bio-compatible composition comprising the steps of:
   providing a curable biocompatible composition in a container having at least a portion that permits transmission of an acoustic signal therethrough;
   directing an acoustic signal to the composition through the portion of the container;

measuring the magnitude of a reflected component of the acoustic signal; and correlating the magnitude to an operating state of the composition wherein the operating state includes dough time, end of working time, and setting time.

2. The method of claim 1, wherein the operating state is time dependent and the measuring and correlating steps occur at period time intervals.

3. The method of claim 1, further comprising the step of providing a signal when the magnitude of the reflected component correlates to a pre-determined operating state of the composition.

4. The method of claim 1, wherein the step of providing a signal includes providing a signal at the end of working time.

5. The method of claim 3, wherein the signal is a visual indicator light.

6. The method of claim 1, wherein the step of measuring the magnitude includes measuring the speed of sound through the composition of the reflected component of the acoustic signal.

7. The method of claim 1, wherein:

the step of directing an acoustic signal occurs at the portion of the container; and the step of measuring the magnitude includes;

providing an acoustic sensor at the portion of the container;

measuring the time for a reflected component reflected at the interface between the container and the composition;

measuring the time for a reflected component reflected at an interface between the composition and a portion of the container opposite the portion through which the acoustic signal is transmitted; and calculating the speed of sound through the composition using the difference between the two measured times.

8. The method of claim 1, wherein the step of measuring the magnitude includes measuring the amplitude of the reflected component.

9. The method of claim 1, wherein the container is a delivery device for delivery of the curable composition to a site in the body.

10. A method for determining the operating state of a curable bio-compatible composition comprising the steps of:

providing a curable biocompatible composition in a container having at least a portion that permits transmission of stable acoustic signals therethrough;

directing an acoustic signal to the composition through the portion of the container;

measuring a value of a transmitted component of the acoustic signal passing through the composition; and correlating the value to an operating state of the composition wherein the operating state includes dough time, end of working time, and setting time.

11. The method of claim 10, wherein the operating state is time dependent and the measuring and correlating steps occur at period time intervals.

12. The method of claim 10, further comprising the step of providing a signal when the magnitude of the transmitted component correlates to a pre-determined operating state of the composition.

13. The method of claim 10, wherein the step of providing a signal includes providing a signal at the end of working time.

14. The method of claim 12, wherein the signal is a visual indicator light.

15. The method of claim 10, wherein the step of measuring the magnitude includes measuring the speed of sound through the composition of the transmitted component of the acoustic signal.

16. The method of claim 10, wherein the step of measuring the magnitude includes;

providing an acoustic sensor at a portion opposite the portion through which the acoustic signal is directed, the opposite portion permitting transmission of an acoustic signal therethrough;

measuring the time for the transmitted component to reach the sensor; and calculating the speed of sound through the composition using the measured time.

17. The method of claim 10, wherein the step of measuring the magnitude includes measuring the amplitude of the reflected component.

18. The method of claim 10, wherein the container is a delivery device for delivery of the curable composition to a site in the body.

19. A method comprising the steps of:

directing an acoustic signal to a curable biocompatible composition located in a container through a portion of said container;

sensing a reflected signal in response to said directing step;

comparing said reflected signal sensed in said sensing step to a set of stored values; and generating a comparison signal indicative of a predicted amount of time remaining until an end of working time of said composition is reached.

20. The method of claim 19, wherein said set of stored values are derived empirically.

21. The method of claim 19, further comprising the step of displaying a visual indication of said predicted amount of time remaining in response to said generating step.

22. The method of claim 21, wherein said visual indication is displayed on a display device.

23. The method of claim 19, further comprising the step of generating an audible indication of said predicted amount of time remaining in response to said generating step.

24. The method of claim 23, wherein said audible indication is generated with a speaker.

* * * * *

UNITED STATES PATENT AND TRADEMARK OFFICE
CERTIFICATE OF CORRECTION

| | | |
|---|---|---|
| PATENT NO. | : 7,618,820 B2 | Page 1 of 1 |
| APPLICATION NO. | : 10/881802 | |
| DATED | : November 17, 2009 | |
| INVENTOR(S) | : Sherman et al. | |

It is certified that error appears in the above-identified patent and that said Letters Patent is hereby corrected as shown below:

On the Title page,

[*] Notice:   Subject to any disclaimer, the term of this patent is extended or adjusted under 35 USC 154(b) by 885 days Delete the phrase "by 885 days" and insert -- by 1491 days --

Signed and Sealed this

Thirty-first Day of August, 2010

David J. Kappos
*Director of the United States Patent and Trademark Office*